(12) United States Patent
Strader (10) Patent No.: US 7,013,222 B2
(45) Date of Patent: Mar. 14, 2006

(54) WAFER EDGE INSPECTION DATA GATHERING

(75) Inventor: Nathan N. Strader, Portland, OR (US)

(73) Assignee: LSI Logic Corporation, Milpitas, CA (US)

( * ) Notice: Subject to any disclaimer, the term of this patent is extended or adjusted under 35 U.S.C. 154(b) by 24 days.

(21) Appl. No.: 10/661,013

(22) Filed: Sep. 12, 2003

(65) Prior Publication Data

US 2005/0060104 A1    Mar. 17, 2005

(51) Int. Cl.
| G01N 31/00 | (2006.01) |
| G01B 5/28 | (2006.01) |
| H01L 21/00 | (2006.01) |
| G01R 31/26 | (2006.01) |

(52) U.S. Cl. .................. 702/30; 702/35; 702/36; 438/12; 438/14

(58) Field of Classification Search .................. 702/30, 702/33–36, 81–84; 714/724, 733; 438/10, 438/12, 14
See application file for complete search history.

(56) References Cited

U.S. PATENT DOCUMENTS

| 6,062,084 A | 5/2000 | Chang et al. |
| 6,545,752 B1 | 4/2003 | Swan et al. |
| 6,566,673 B1 | 5/2003 | Swan et al. |
| 6,799,130 B1 * | 9/2004 | Okabe et al. .................. 702/82 |
| 2002/0111038 A1 * | 8/2002 | Matsumoto et al. ........ 438/763 |

* cited by examiner

Primary Examiner—Bryan Bui
Assistant Examiner—Meagan S Walling
(74) Attorney, Agent, or Firm—L. Jon Lindsay (57) ABSTRACT

A wafer edge inspection method and apparatus include a review tool that captures images of the semiconductor wafer. According to various embodiments, the present invention also includes a map of points of interest proximate to the edge of the wafer, automatic image capturing at the points of interest, fake defect locations defining the points of interest, a database in which the images are stored and computer-searchable for detailed defect analysis, a software tool for controlling the method and apparatus and/or context information identifying the points of interest, the inspected wafer and/or the fabrication station/step preceding the inspection.

17 Claims, 5 Drawing Sheets

WAFER EDGE INSPECTION DATA GATHERING

CROSS-REFERENCE TO RELATED APPLICATION

This invention is related to an invention for Wafer Edge Defect Inspection, described in U.S. patent application Ser. No. 10/628614, filed Jul. 28, 2003, which is assigned to the assignee of the present invention. The subject matter of this application is incorporated herein by this reference.

FIELD OF THE INVENTION

This invention relates to inspection of semiconductor wafers on which are formed integrated circuits (ICs). In particular, this invention relates to new and improved techniques for gathering data from inspection of the edges of the wafers.

BACKGROUND OF THE INVENTION

A significant trend throughout IC development has been to try to increase the "yield rate" of semiconductor fabrication systems. The yield rate refers to the percentage of usable IC's produced by a fabrication system compared to the total number attempted. Similarly, the yield rate may refer to the percentage of usable IC's obtained on average from a semiconductor wafer that is processed through the fabrication system. A semiconductor wafer is essentially a thin disc of highly purified semiconductor material on which many IC's are fabricated together and then separated for individual packaging.

Significant factors that can negatively impact the yield rate are the number and size of defects in the wafer. Defects may include cracks, crazes (i.e. microscopic cracks), chips, flakes, scratches, marks, missing/broken edges and particle and residue contamination, among others.

Defects are particularly detrimental to the yield rate when they occur on the top surface of the wafer, since the top surface is the region where the IC's are formed on the wafer. Of historically lesser concern have been any other areas of the wafer, such as the bottom surface and the edge, or bevel, of the wafer. Since these areas are further from the formation of the IC's, any defects therein have been considered to have less of an impact on the yield rate for the IC's. Thus, many wafer-inspection and defect-detection techniques have been developed to inspect for defects in the top surface of wafers; whereas, comparatively few techniques have been developed to inspect for defects elsewhere on the wafers.

Figure 1:
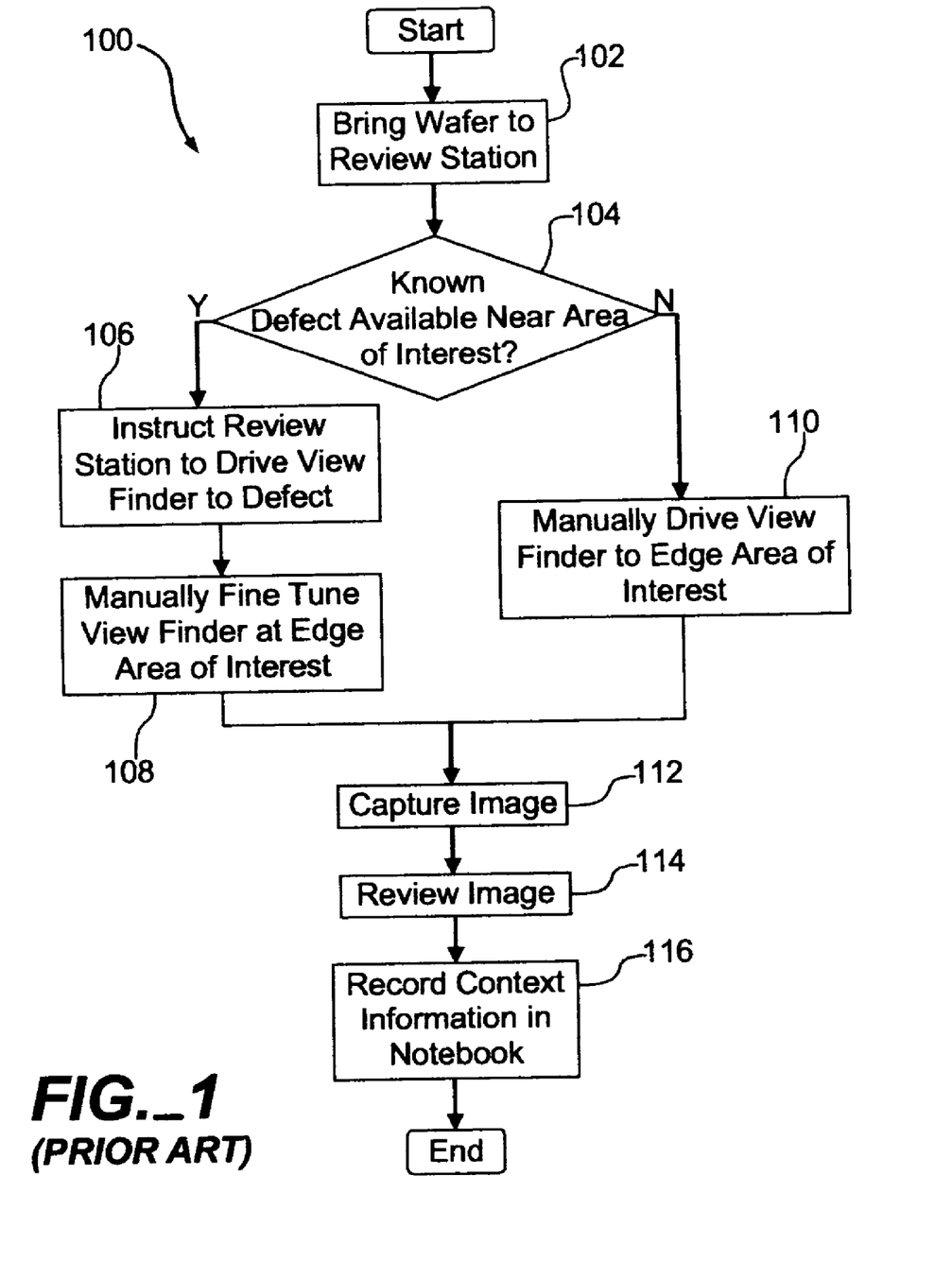
FIG. 1 is a flowchart of a prior art procedure for wafer edge inspection.

Detailed computerized image-analysis techniques have been used for wafer top surface defect detection, but not for wafer edge defect detection, since it has been commonly considered unnecessary to do so. Instead, wafer edge inspection has primarily been performed by manual visual inspection by a worker in the fabrication plant as illustrated by a flow chart shown in FIG. 1 for an exemplary manual visual inspection procedure 100. After a wafer is brought to a review station (step 102) for inspection, the worker determines (step 104) whether there is a known defect, such as a defect in the top surface of the wafer, near an area of interest on the edge of the wafer. The area of interest, in this case, is a point at or near the edge of the wafer where the worker desires to inspect for an edge defect. A positive answer at step 104 is helpful because currently available review tools enable the worker to instruct the review tool to automatically drive a view finder for an image capturing device to the known defect (step 106). This step (106) serves as a simple "gross" adjustment for the view finder. The worker then "fine tunes" the location of the view finder to the edge area of interest (step 108). If there is no known defect near the area of interest (as determined at step 104), then the worker must manually drive the view finder (step 110) to the edge area of interest without the benefit of the automatic gross adjustment of step 106. In either case, some manual adjustment of the view finder must be performed, which is time consuming and error prone. The image capturing device, such as a high-resolution camera, may then be used to generate an image (step 112) of the wafer edge on a monitor, which the worker manually views (step 114) for defects. In a lab notebook, the worker then records (step 116) the type of defect observed along with "context" information, such as lot ID, wafer ID, defect location, the step in the over-all fabrication process through which the wafer has just been processed, etc. This inspection procedure 100 is in stark contrast to the various complex computerized image-analysis techniques, among other inspection techniques, that have been developed to inspect the top surface of the wafers.

The generated images of the wafer edge are typically saved to a laser disk after manual viewing. The written notes regarding how the images can be extracted from that disk are kept only in the lab notebooks. Thus, there is typically no computer-searchable image or defect data.

Current non-visual wafer edge inspection techniques may record data "plots" (not images), which the worker may review for indications of defects or a computer may analyze for possible defects. Though the data may be stored for a time, the purpose of the data is generally for immediate pass/fail analysis of the wafer, so the wafer may be passed on for further processing, discarded as unusable or rerouted for rework or repair.

It is with respect to these and other considerations that the present invention has evolved.

SUMMARY OF THE INVENTION

The present invention arose out of the recognition of the importance of wafer edge defects relative to yield rate and the need to give greater consideration to edge defects during wafer fabrication. It was realized that defects at the edge of a wafer, though they may be far from most of the IC's on the surface of the wafer, frequently cause problems in the fabrication of the IC's. As processing technology has improved, though, the usable area of the wafer for fabricating IC's is now about 2 mm from the edge of the wafer. This proximity of the IC's to the edge of the wafer has largely caused a renewed focus on edge defect issues. Therefore, a need has been recognized for an improved wafer edge inspection technique that goes beyond the limited capabilities of the inspection techniques described above, which have proven to be too time-consuming and unreliable to adequately address the problem of wafer edge defects during the over-all fabrication process. The aforementioned patent application describes such an improved wafer edge inspection technique.

The present invention includes improved systems of and methods for gathering inspection data for a wafer edge inspection technique, such as the one described in the aforementioned patent application. Adequate gathering, storing and managing of inspection data is necessary for future analysis of the data in order to perform a detailed investigation of the efficiency of the over-all fabrication system so that each process step within the fabrication system may be optimized and the yield rate maximized. The wafer edge inspection techniques heretofore developed do not include such a data-gathering feature.

Accordingly, the present invention preferably involves methods for gathering semiconductor wafer edge inspection data and systems or apparatuses for automated inspection of the semiconductor wafer edge. Generally, one or more points of interest on the edge of the wafer are supplied to a review tool, which is instructed to capture images at those points on the wafer edge. According to some particular embodiments of the present invention, the points of interest are supplied in automatic succession to the review tool, so the images at each of the points of interest may be captured rapidly and stored automatically. The speed of data gathering thus enabled allows for a much for efficient operation than the manual procedures described in the background.

Additionally, according to certain embodiments, the captured images are preferably automatically correlated with the points of interest at which the images were taken. Thus, the captured images can be quickly located or identified, without resorting to handwritten notes in a lab notebook.

In other embodiments, the points of interest are indicated by fake defect locations, and the review tool is instructed to capture the images at the fake defects. In other particular embodiments, the review tool is preferably capable of driving the view finder of the image capturing device to a known defect, so the fake defect locations enable automated repositioning of the view finder on-the-fly in order to capture images at a variety of locations at or near the wafer edge without manual intervention.

According to other embodiments, the captured images are correlated with "context information" that preferably identifies the wafer from which the images were taken. Additional embodiments preferably include in the context information an identification of the fabrication process step performed on the wafer prior to capturing the images or gathering the inspection data. Additionally, the context information may preferably be computer-searchable, so that future data analysis may quickly search through the stored images captured from the same wafer after different fabrication process steps or captured from different wafers after the same process step. With this capability, an improved wafer edge inspection technique, such as the one described in the aforementioned patent application, may have highly efficient data searching, managing and analyzing features that are unavailable with the limited capabilities of the inspection techniques described in the background.

In other embodiments, a software tool is connected to, or in communication with, the review tool to supply the instructions to the review tool to perform the image capture. According to various embodiments, the software tool may also preferably control various functions of the inspection system or various steps of the methods, including those features that enable the automation of the data gathering, storing and managing.

A more complete appreciation of the present invention and its scope, and the manner in which it achieves the above noted improvements, can be obtained by reference to the following detailed description of presently preferred embodiments of the invention taken in connection with the accompanying drawings, which are briefly summarized below, and the appended claims.

DETAILED DESCRIPTION

Figure 2:
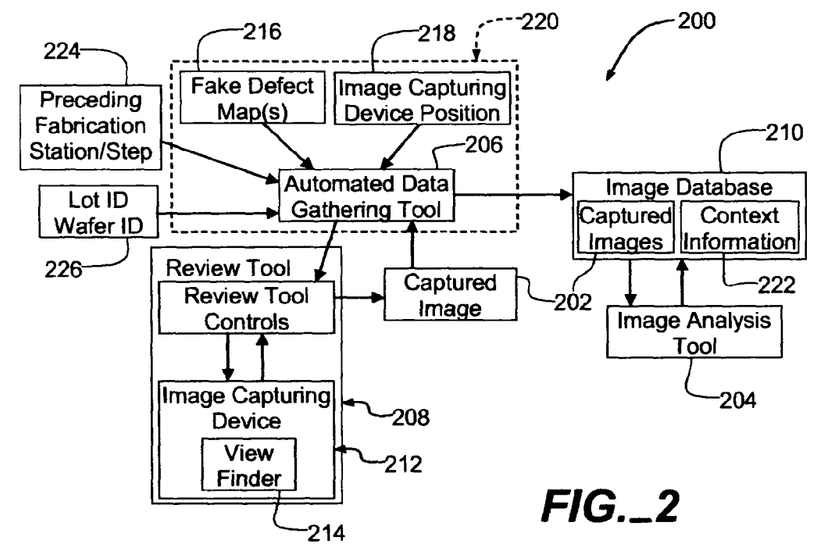
FIG. 2 is a simplified schematic of a wafer edge inspection system incorporating the present invention.

An exemplary wafer edge inspection system 200, as shown in FIG. 2, generally captures images 202 of the edge of a wafer (not shown), such as a semiconductor wafer used in the fabrication of integrated circuits, for detailed computer analysis thereof by an image analysis tool 204. The image analysis tool 204 generally analyzes the captured images 202 as described in the aforementioned patent application.

In addition to the image analysis tool 204, the wafer edge inspection system 200 generally includes an automated data gathering tool 206, a conventional review tool 208 and an image database 210. The automated data gathering tool 206, the review tool 208 and the image database 210 generally function together to automate the data capture, storage and management for the wafer edge inspection system 200.

The review tool 208 generally includes wafer inspection hardware, such as an image capturing device 212 having a view finder 214. The review tool 208 generally receives the wafers (not shown) to be inspected and captures the images 202 of portions thereof with the image capturing device 212.

The automated data gathering tool 206 is generally a software tool for controlling the automated wafer inspection and data gathering functions of the wafer edge inspection system 200. Thus, the automated data gathering tool 206 connects to, or is in communication with, the review tool 208 to supply operating instructions to the review tool 208 and to receive the data generated thereby, i.e. the captured images 202. The automated data gathering tool 206 also connects to the image database 210 to transfer the captured images 202 thereto for automatic storage and later analysis by the image analysis tool 204.

The automated data gathering tool 206 generates the operating instructions for the review tool 208 according to "points of interest" on the edge of the wafer (not shown) at which it is desired to capture the images 202. The review tool 208 is preferably a conventional type that can capture an image of the wafer at locations identified by known defects. Thus, in a preferred embodiment of the present invention, in order to cause the review tool 208 to automatically capture the images 202 at the points of interest on the edge of the wafer, the points of interest are identified by fake defect locations and identifiers for the fake defect locations are supplied by the automated data gathering tool 206 to the review tool 208.

The review tool 208 is also preferably the conventional type described in the background, wherein the review tool 208 can perform the "gross" adjustment of the position of the view finder 214 of the image capturing device 212 by driving the view finder 214 to a known defect. According to particular embodiments of the present invention, however, instead of following the gross adjustment by manual adjustment of the view finder 214 to the actual point of interest, the review tool 208 is caused to drive the view finder 214 directly to the points of interest according to the fake defect location identifiers.

According to another particular embodiment, the fake defect location identifiers are preferably consolidated in a radial "map" 216 of coordinates for the fake defect locations. The fake defect map 216 is effectively a combination of the fake defect location identifiers giving the locations of the fake defects on the edge of the wafer (not shown) in the order in which the fake defect locations would be encountered by the image capturing device 212 as the wafer rotates. The fake defect map 216 thus defines the points of interest at which the images 202 are to be captured on a given wafer. Using the fake defect map 216 for the current wafer, the automated data gathering tool 206 automatically supplies the fake defect location identifiers to the review tool 208, in order for the review tool 208 to capture the images 202 at all of the points of interest in automatic succession. Optionally, the automated data gathering tool 206 may also supply information 218 to the review tool 208 specifying the position of the image capturing device 212. The image capturing device position information 218 may include both the location and the angle at which the image capturing device 212 is to be positioned. The fake defect maps 216 and the image capturing device position information 218 will be described in greater detail below with reference to FIGS. 4–8. Additionally, the automated data gathering tool 206, the fake defect maps 216 and the image capturing device position information 218 are shown surrounded by a dashed block 220 because they may optionally be combined in a single software tool.

An improvement and advantage of some embodiments of the present invention is that the automated data gathering tool 206 also correlates the captured images 202 with context information 222 and stores the context information 222 in a computer-searchable manner in the image database 210 along with the captured images 202. The context information 222 is generally formed by the automated data gathering tool 206 from the fake defect maps 216, the image capturing device position information 218, preceding fabrication station/step information 224 (described below with reference to FIG. 3) and/or conventional lot ID and wafer ID information 226. In this manner, any of the captured images 202 is searchable and locatable within the database 210 by the image analysis tool 204 according to each of the types of context information 222 in order to perform detailed analysis of any given wafer (not shown), any given fabrication station/step or the over-all fabrication system or fabrication plant (not shown).

Figure 3:
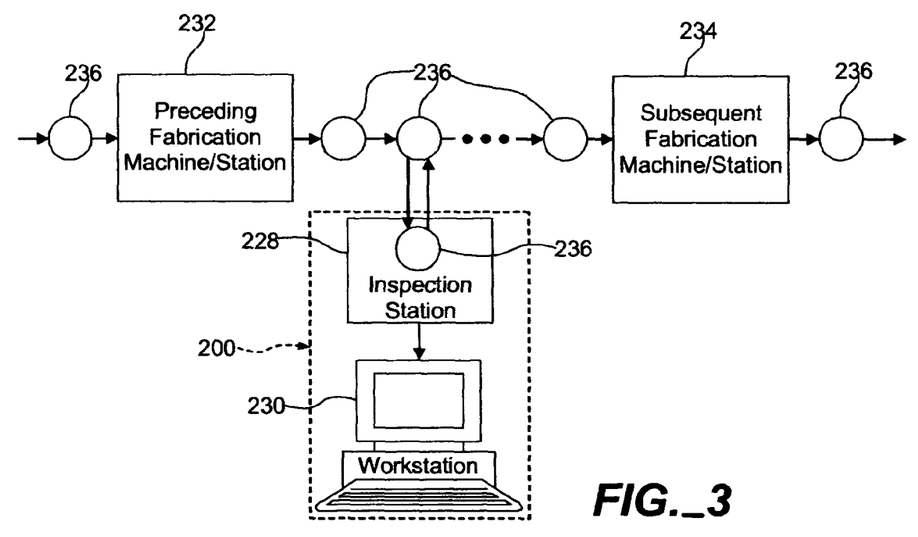
FIG. 3 is a simplified block diagram of a portion of a fabrication system including the wafer edge inspection system shown in FIG. 2.

The wafer edge inspection system 200 preferably involves an inspection station 228 and a workstation 230 connected together, as shown in FIG. 3. The inspection station 228 is interposed between a preceding fabrication station 232 and a subsequent fabrication station 234 to receive some or all of the wafers 236 passing from the preceding fabrication station 232 to the subsequent fabrication station 234. Exemplary embodiments for the inspection station 228 are shown in FIGS. 3, 4 and 5 of the aforementioned patent application. The workstation 230 may be physically located away from the inspection station 228 and the fabrication stations 232–234, since the workstation 230 does not have to be within a clean-room environment as required for the parts of the over-all fabrication system (not shown) that handle the wafers 236.

The workstation 230 is preferably a conventional general-purpose computer on which the automated data gathering tool 206 (FIG. 2) may operate to control the inspection station 228. The inspection station 228 preferably includes the review tool 208 (FIG. 2), as well as wafer-handling hardware (not shown), in order to receive the wafers 236 and generate the captured images 202 (FIG. 2) from the wafers 236.

Using the workstation 230, a worker controls the inspection procedure. In other words, the worker generates the fake defect map 216 (FIG. 2) or selects the fake defect map 216 from pre-formed fake defect maps or instructs the automated data gathering tool 206 (FIG. 2) to generate a "sampling plan," or list of fake defects. Similarly, the worker also generates the image capturing device position information 218 (FIG. 2). Alternatively, the worker simply selects a pre-formed data gathering procedure, which includes all of the required information (i.e. the fake defect map 216 and the image capturing device position information 218) for the desired inspection procedure. Then the worker instructs the automated data gathering tool 206 to perform the inspection procedure. The automated data gathering tool 206 then functions as described above to initiate the inspection procedure by supplying the fake defect information to the review tool 208 (FIG. 2). The review tool 208 captures the images 202 (FIG. 2). The captured images 202 and the context information 222 are then stored in the database 210.

Later, preferably also using the workstation 230, the worker accesses the stored data for one or more wafers and one or more process steps and instructs the workstation 230 to perform various edge defect analyses as described in the aforementioned patent application. To perform these analyses, it is necessary to maintain the inspection data within the database 210 (FIG. 2) for every wafer 236 for a proper amount of time. In fact, the worker may not instruct the workstation 230 to perform these analyses until several minutes or hours or even days after the data has been generated, so the database 210 may have to store the data indefinitely.

Figure 4:
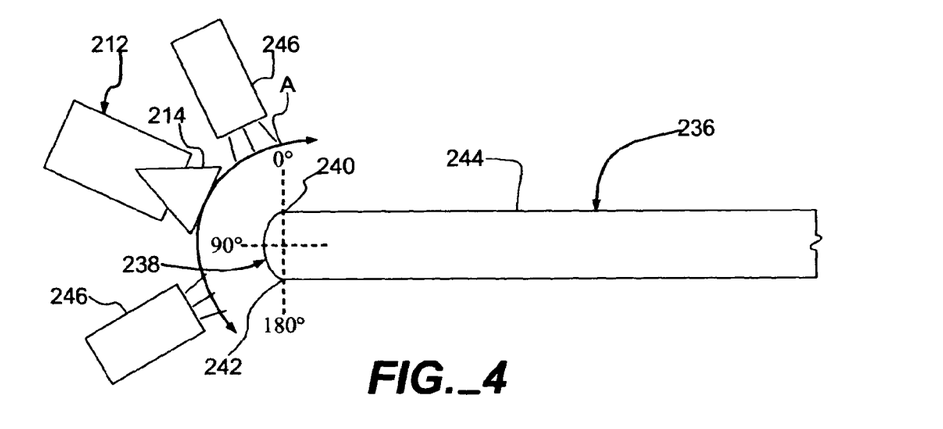
FIG. 4 is a simplified elevation view of a wafer to be processed by the portion of the fabrication system shown in FIG. 3 and an image capturing device incorporated in the wafer edge inspection system shown in FIG. 2.

A typical wafer 236, as shown in FIG. 4, has an edge, or bevel, 238 with a slight convex curvature. The top 240 and bottom 242 (at approximately 0° and 180°, respectively, of the curvature) of the edge 238 have a smaller radius of curvature than does the middle of the edge 238. The primary area of interest for edge inspection extends from a point on the top surface 244 of the wafer 236 is slightly interior of the top 240 of the edge 238 to a point slightly exterior of the bottom 242 of the edge 238, or any portion thereof, as indicated by the arrow A. The image capturing device 212, therefore, may have a field of view from the view finder 214 that incorporates the entire desired inspection area, or may be positioned relative to the edge 238 along the arrow A to any angle at which a desired portion of the edge 238 is to be scanned. This positioning is preferably defined by the image capturing device position information 218 (FIG. 2).

The image capturing device 212 automatically scans the desired portion of the edge 238 of the wafer 236 and captures an image thereof. The image capturing device 212 preferably does this procedure according to a "recipe" that specifies various parameters that affect the image that will be captured. For instance, the recipe may include values for: the angle of the image capturing device 212 relative to the edge 238 of the wafer 236 along arrow A, the magnification of the image capturing device 212, the focus of the image capturing device 212 (given the curvature of the edge 238, every point in the area of interest may not be in focus at the same time), the brightness of one or more illumination sources 246 that illuminate the edge 238 of the wafer 236 in the case that the image capturing device 212 is an optical device, the portion of the edge 238 of the wafer 236 to be scanned (e.g. portion of arrow A), the rotational speed of the wafer 236, a gain setting on a photomultiplier sensor, contrast setting, the accelerating voltage for an electron beam and probe current in the event that the image capturing device 212 is a scanning electron microscope, the angular location of the desired sample area, and threshold values for determining a defect, among other possible parameters for the inspection recipe. The recipe may be stored in the database 210 (FIG. 2) as part of the context information 222 (FIG. 2) for each wafer 236 scanned, so the later image analysis can take into account any of these parameters.

Figure 5:
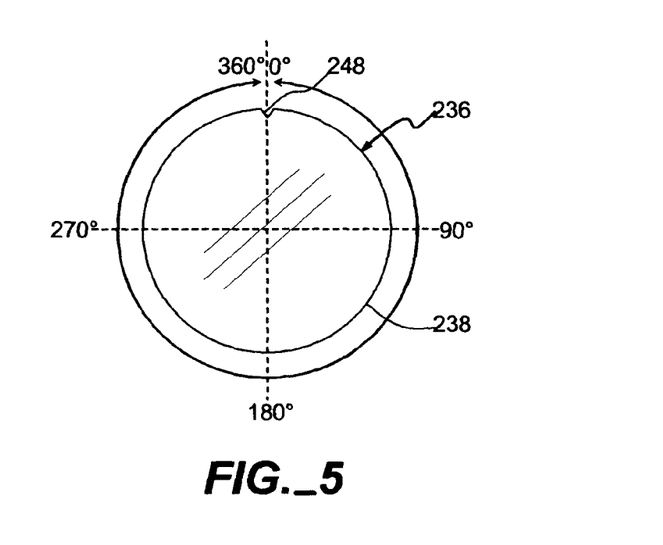
FIG. 5 is a simplified plan view of a wafer to be processed by the portion of the fabrication system shown in FIG. 3 and inspected by the wafer edge inspection system shown in FIG. 2.

Each wafer 236, as shown in FIG. 5, includes an orientation location point, such as a notch 248, etc. The inspection station 228 (FIG. 3) locates the notch 248 to orient the wafer 236 and then scans the edge 238 of the wafer 236 as the wafer 236 rotates either for a full 360° from the notch 248 back to the notch 248 or for some smaller inspection area, such as a 90° or 180° section or some other range depending on whatever portion of the wafer 236 needs to be inspected as described below with reference to FIGS. 6–8. The image capturing device 212 (FIGS. 2 and 4) then captures an image 202 (FIG. 2) of the desired inspection area and the captured image 202 is transferred to the database 210 (FIG. 2).

Figure 6:
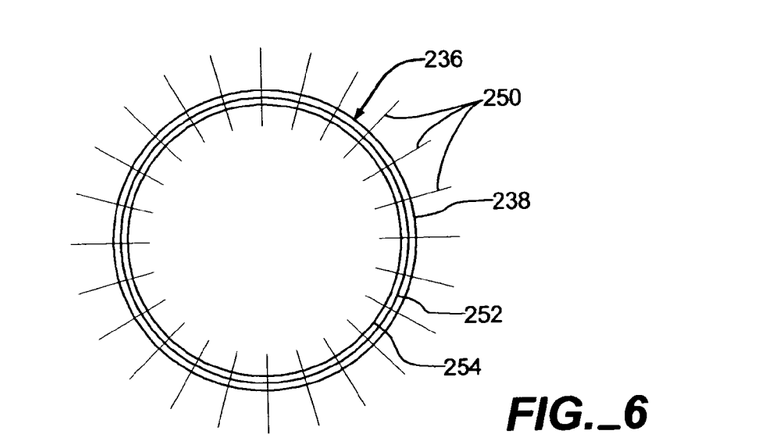
FIGS. 6, 7 and 8 are simplified plan views of wafers to be inspected by the wafer edge inspection system shown in FIG. 2 illustrating alternative embodiments for designating points of interest on the wafer edge.
Figure 7:
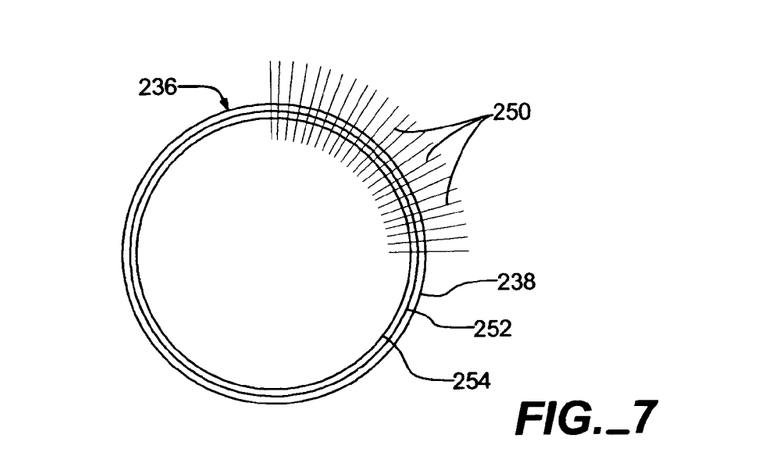
Figure 8:
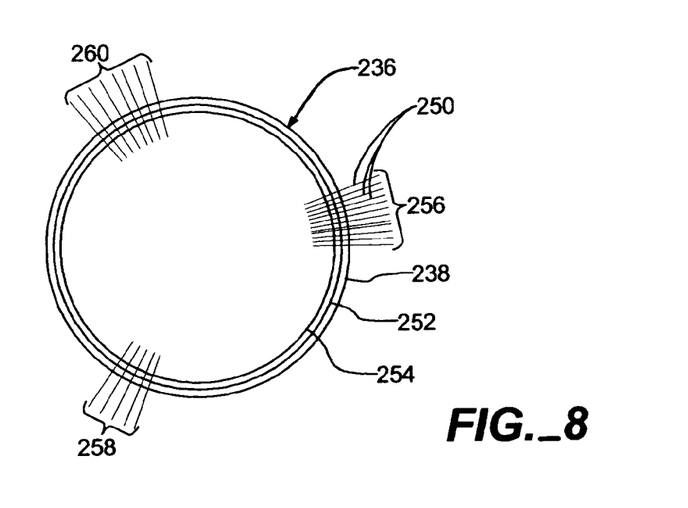

Three exemplary fake defect maps 216 (FIG. 2) are illustrated by FIGS. 6, 7 and 8. The fake defect locations, or points of interest, are indicated by radial lines 250 at the edge 238 of the wafer 236. The location of the fake defects relative to the edge 238 of the wafer 236 are indicated by concentric circle 252 or 254 or by the edge 238, itself. Alternatively, the designation of the location of the fake defects relative to the edge 238 (i.e. the concentric circle 252 or 254 or the edge 238) may be effectively included in the image capturing device position information 218 (FIG. 2), rather than in the fake defect map 216.

FIG. 6 illustrates a fake defect map 216 (FIG. 2) with which images 202 (FIG. 2) around the entire circumference of the wafer 236 may be captured. The radial lines 250 are evenly spaced throughout the entire edge 238 of the wafer 236. Thus, if the image capturing device 212 (FIGS. 2 and 4) has a sufficiently wide angle view, then the images 202 captured at each point of interest (indicated by the radial lines 250) could extend on either side of the point of interest halfway to the previous or subsequent point of interest. Thereby, the entire edge 238 could be included in the captured images 202.

FIG. 7 illustrates a fake defect map 216 (FIG. 2) with which images 202 (FIG. 2) around an approximately 90-degree portion of the circumference of the wafer 236 may be captured. Additionally, since the radial lines 250 are shown closer together than in FIG. 6, the region on either side of the points of interest included in the captured images 202 may be much smaller, and the resolution of the captured images 202 may be much greater. Thereby, the desired portion of the edge 238 of the wafer 236 can be imaged with much greater detail or clarity.

FIG. 8 illustrates a fake defect map 216 (FIG. 2) with which images 202 (FIG. 2) at more than one non-contiguous region 256, 258 and 260 around the circumference of the wafer 236 and at more than one resolution may be captured.

The form of the fake defect map 216 chosen for any given wafer 236 or any given wafer edge inspection system 200 may depend on experience, experiment or expectation. Thus, if experience indicates that a given fabrication station (e.g. 232 in FIG. 3) frequently results in edge defects in region 256, then this region 256 may be included in the fake defect map 216. On the other hand, if the locations of defects caused by the given fabrication station 232 are random or unknown, then the fake defect map 216 illustrated in FIG. 6 for capturing images of the entire edge 238 of the wafer 236 may be used. Additionally, if the given fabrication station 232 results in defects that are very small or difficult to detect, then the closer spacing of the fake defect locations (i.e. the radial lines 250) along with the higher resolution of the image capturing device 212 (FIGS. 2 and 4) may be used.

Figure 9:
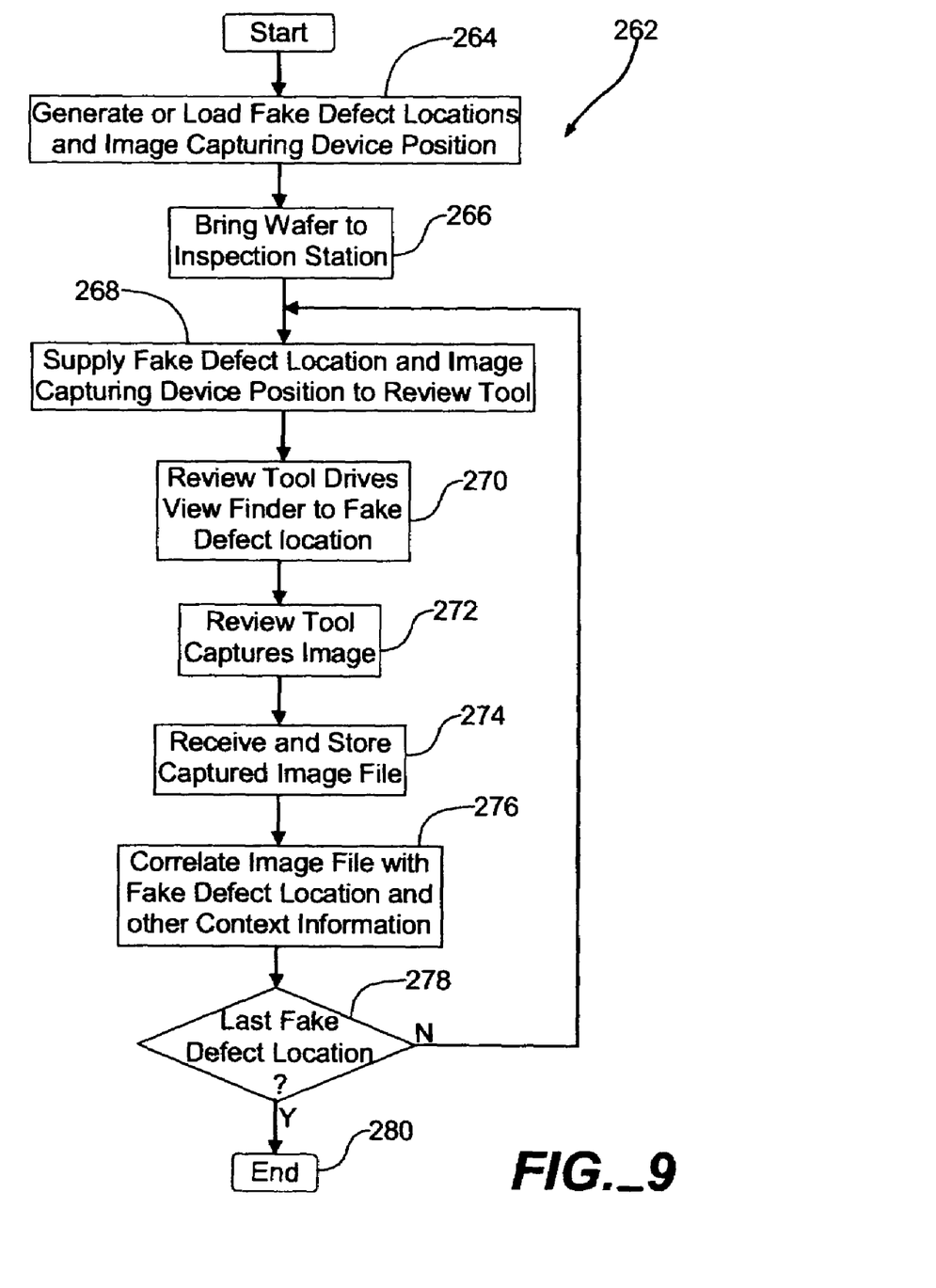
FIG. 9 is a flowchart of a simplified procedure for performing wafer edge inspection by the wafer edge inspection system shown in FIG. 2.

An exemplary wafer inspection data gathering procedure 262 performed by the wafer edge inspection system 200 (FIG. 2) is shown in FIG. 9. The fake defect location identifiers (i.e. the fake defect map 216, FIG. 2) and the image capturing device position information 218 (FIG. 2) are generated or loaded from existing information at step 264 by the automated data gathering tool 206 (FIG. 2). A selected wafer 236 (FIG. 3) is then brought to the inspection station 228 (FIG. 3) at step 266. The first fake defect location identifier and the image capturing device position information 218 are supplied to the review tool 208 (FIG. 2) at step 268. The review tool 208 then drives the view finder 214 (FIG. 2) of the image capturing device 212 (FIGS. 2 and 4) to the first fake defect location at step 270. In a particular embodiment, step 270 preferably involves only positioning the view finder 214 at the desired location and viewing angle along arrow A (FIG. 4), or at the concentric circle 252 or 254 (FIGS. 6–8) or the edge 238 (FIGS. 4–8) of the wafer 236. The review tool 208 then captures (step 272) the image 202 (FIG. 2) at the first fake defect location (i.e. the first radial line 250, FIGS. 6–8), preferably when the first fake defect location aligns with the view finder 214 as the wafer 236 is being rotated through each of the radial lines 250. The automated data gathering tool 206 then receives (step 274) the captured image 202 and transfers the captured image 202 to the database 210 (FIG. 2) for storage. The automated data gathering tool 206 (at step 276) generates the context information 222 (FIG. 2) as described above, correlates the context information 222 with the captured image 202 and stores the context information 222 with the captured image 202 in the database 210. The automated data gathering tool 206 (at step 278) then determines whether the current fake defect location is the last fake defect location. If not, then the procedure 262 returns to step 268 to supply the next fake defect location to the review tool 208. In a particular embodiment, each of the fake defect locations are at the same concentric circle 252 or 254 or at the edge 238 of the wafer 236, so the image capturing device position information 218 does not have to be re-supplied to the review tool 208 at step 268 and the view finder 214 does not have to be moved at step 270. The other steps 272, 274 and 276 are repeated for each fake defect location until the last fake defect location has been inspected, as determined at step 278. The procedure 262 then ends at step 280 for the current wafer 236, and is repeated for the next wafer 236.

It is apparent from the previous description that the present invention enables a robust wafer edge defect inspection system. The inspection has the advantage of being automated, so control is achieved simply by adjusting the fake defect maps 216 (FIG. 2), the image capturing device position information 218 (FIG. 2) and the inspection recipe. The inspection information (i.e. the captured images 202, FIG. 2) is stored and readily accessible for any desired analysis at any time on any inspected wafer(s). The computer-searchable context information 222 (FIG. 2) enables later rapid recovery of any part of the inspection information. Thus, the user can perform a detailed analysis on many parts of the fabrication system after the fabrication system has been in operation for any length of time in order to ensure proper functioning of the fabrication system or debugging of potential problems that any arise upon initial assembly of the fabrication system or at any other line.

Presently preferred embodiments of the present invention and many of its improvements have been described with a degree of particularity. This description is of preferred examples of implementing the invention, and is not necessarily intended to limit the scope of the invention. The scope of the invention is defined by the following claims.

The invention claimed is:

1. A method of gathering semiconductor wafer edge inspection data, wherein a review tool captures images of the semiconductor wafer, comprising:
   providing a semiconductor wafer;
   generating a map of points of interest proximate to an edge of the semiconductor wafer;
   identifying the points of interest with location identifiers for fake defects at the points of interest;
   supplying the points of interest to the review tool in automatic succession;
   instructing the review tool to capture images at the points of interest;
   automatically storing the captured images; and
   correlating the captured images with the points of interest.

2. A method as defined in claim 1 further comprising:
   generating context information for the captured images identifying the semiconductor wafer; and
   correlating the captured images with the context information.

3. A method of gathering semiconductor wafer edge inspection data, wherein a review tool captures images of the semiconductor wafer, the review tool is incorporated in a semiconductor fabrication system having a plurality of fabrication stations for performing fabrication steps on the semiconductor wafer, and the review tool is situated subsequent to a preceding one of the fabrication stations, comprising:
   providing a semiconductor wafer;
   generating a map of points of interest proximate to an edge of the semiconductor wafer;
   supplying the points of interest to the review tool in automatic succession;
   instructing the review tool to capture images at the points of interest;
   automatically storing the captured images;
   correlating the captured images with the points of interest;
   generating first context information for the captured images identifying the semiconductor wafer;
   correlating the captured images with the first context information;
   generating second context information for the captured images identifying the preceding fabrication station; and
   correlating the captured images with the second context information.

4. A method of gathering semiconductor wafer edge inspection data, wherein a review tool captures images of the semiconductor wafer, comprising:
   providing a semiconductor wafer;
   generating points of interest proximate to an edge of the semiconductor wafer by identifying fake defects with fake defect identifiers;
   causing the review tool to capture images at the points of interest by instructing the review tool to capture the images at the fake defects identified by the fake defect identifiers; and
   storing the captured images.

5. A method as defined in claim 4 wherein the review tool captures images of the semiconductor wafer through a view finder and can drive the view finder to an identified defect location, further comprising:
   supplying the fake defect identifiers to the review tool; and
   instructing the review tool to drive the view finder to the fake defects identified by the fake defect identifiers and to capture images at the fake defects.

6. A method as defined in claim 5 further comprising:
   correlating the captured images with the points of interest according to the fake defect at which each captured image was captured.

7. A method as defined in claim 4 further comprising:
   generating context information including information identifying the semiconductor wafer; and
   correlating the captured images with the context information.

8. A method of gathering semiconductor wafer edge inspection data, wherein a review tool captures images of the semiconductor wafer, the review tool is incorporated in a semiconductor fabrication system having a plurality of fabrication stations for performing fabrication steps on the semiconductor wafer, and the review tool is situated subsequent to a preceding one of the fabrication stations, comprising:
   providing a semiconductor wafer;
   generating first context information including information identifying the semiconductor wafer;
   generating a map of points of interest proximate to an edge of the semiconductor wafer;
   instructing the review tool to capture images at the points of interest;
   storing the captured images;
   correlating the captured images with the points of interest and the first context information;
   generating second context information for the captured images identifying the preceding fabrication station; and
   correlating the captured images with the second context information.

9. A method as defined in claim 8 further comprising:
   storing the context information in a computer-searchable manner.

10. A method as defined in claim 8 wherein the semiconductor wafer edge inspection data is gathered by a software tool, further comprising:
    the software tool instructing the review tool to capture the images at the points of interest; and
    the software tool correlating the captured images with the points of interest and the context information.

11. A method of gathering semiconductor wafer edge inspection data, wherein a review tool captures images of the semiconductor wafer, the semiconductor wafer edge inspection data is gathered by a software tool, the review tool is incorporated in a semiconductor fabrication system having a plurality of fabrication stations for performing fabrication steps on the semiconductor wafer, and the review tool is situated subsequent to a preceding one of the fabrication stations, comprising:

provide a semiconductor wafer;

generating first context information including information identifying the semiconductor wafer;

generating a map of points of interest proximate to an edge of the semiconductor wafer;

the software tool instructing the review tool to capture images at the points of interest;

storing the captured images;

the software tool correlating the captured images with the points of interest and the first context information;

generating second context information for the captured images identifying the preceding fabrication station; and the software tool correlating the captured images with the second context information.

12. A system for automated inspection of a semiconductor wafer edge comprising:

a review tool having an image capturing device capable of capturing an image of the semiconductor wafer edge;

a software tool connected to the review tool to supply instructions to the review tool to capture an image at a point of interest proximate to the semiconductor wafer edge and to receive the captured image from the review tool; and a database connected to the software tool to receive and store the captured image from the software tool and context information identifying the semiconductor wafer, the context information being correlated with the captured image;

and wherein:

the review tool is capable of capturing the image at a predetermined defect location;

the point of interest is indicated by a predetermined fake defect location identified by a fake defect identifier;

the instructions supplied from the software tool to the review tool include the fake defect identifier; and the review tool captures the image at the predetermined fake defect location.

13. A system for automated inspection of a semiconductor wafer edge as defined in claim 12 wherein:

the review tool is capable of driving the image capturing device to the predetermined defect location; and the review tool drives the image capturing device to the predetermined fake defect location identified by the fake defect identifier in order to capture the image at the predetermined fake defect location.

14. A system for automated inspection of a semiconductor wafer edge as defined in claim 12 wherein:

the context information correlated with the captured image includes the point of interest according to the predetermined fake defect location at which the captured image was captured.

15. A system for automated inspection of a semiconductor wafer edge as defined in claim 12 wherein:

the database, including the context information, is computer-searchable.

16. A system for automated inspection of a semiconductor wafer edge as defined in claim 12 wherein:

the instructions supplied from the software tool to the review tool include a plurality of points of interest at which the review tool captures a plurality of images in automatic succession; and the software tool automatically receives and stores the captured images in the database correlated with the context information for each image.

17. A system for automated inspection of a semiconductor wafer edge for use in a fabrication system having a plurality of fabrication stations including a preceding fabrication station, comprising:

a review tool having an image capturing device capable of capturing an image of the semiconductor wafer edge;

a software tool connected to the review tool to supply instructions to the review tool to capture an image at a point of interest proximate to the semiconductor wafer edge and to receive the captured image from the review tool; and a database connected to the software tool to receive and store the captured image from the software tool and context information identifying the semiconductor wafer, the context information being correlated with the captured image;

and wherein:

the review tool is situated in the fabrication system subsequent to the preceding fabrication station; and the context information further identifies the preceding fabrication station.

* * * * *